United States Patent
Catalan (10) Patent No.: US 7,626,073 B2
(45) Date of Patent: Dec. 1, 2009

(54) HYDROPHOBIC SURFACE COATED ABSORBENT ARTICLES AND ASSOCIATED METHODS

(75) Inventor: Kemal Vatansever Catalan, Anderson Township, OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 11/055,743

(22) Filed: Feb. 10, 2005

(65) Prior Publication Data

US 2005/0177123 A1    Aug. 11, 2005

Related U.S. Application Data

(60) Provisional application No. 60/543,785, filed on Feb. 11, 2004.

(51) Int. Cl.
- A61F 13/15 (2006.01)
- C08G 18/18 (2006.01)
- C08G 18/00 (2006.01)
- C08G 18/38 (2006.01)

(52) U.S. Cl. ............ 604/367; 604/385.04; 604/378; 604/381; 604/385.09; 521/129; 521/167; 521/128

(58) Field of Classification Search ............ 604/385.04, 604/367, 378, 381, 385.09; 521/129, 167, 521/128
See application file for complete search history.

(56) References Cited

U.S. PATENT DOCUMENTS

| | | | |
|---|---|---|---|
| 4,573,986 A | 3/1986 | Minetola et al. | |
| 4,675,015 A * | 6/1987 | Brown | 604/385.09 |
| 4,769,023 A | 9/1988 | Goebel et al. | |
| 4,921,622 A | 5/1990 | Kato et al. | |
| 5,126,189 A * | 6/1992 | Tanny et al. | 428/220 |
| 5,149,576 A | 9/1992 | Potts et al. | |
| 5,151,321 A | 9/1992 | Reeves et al. | |
| 5,171,391 A * | 12/1992 | Chmielewski et al. | 156/229 |
| 5,418,051 A | 5/1995 | Caldwell et al. | |
| 5,473,002 A | 12/1995 | Gardiner et al. | |
| 5,565,564 A | 10/1996 | Kirchner | |
| 5,607,760 A | 3/1997 | Roe | |
| 5,609,587 A | 3/1997 | Roe | |
| 5,635,128 A | 6/1997 | Gardiner et al. | |
| 5,635,191 A | 6/1997 | Roe et al. | |
| 5,643,588 A | 7/1997 | Roe et al. | |
| 5,696,191 A | 12/1997 | Nohr et al. | |
| 5,811,482 A | 9/1998 | Sabia et al. | |
| 5,885,656 A | 3/1999 | Goldwasser | |
| 6,150,020 A | 11/2000 | Dharmadhikary et al. | |
| 6,160,148 A | 12/2000 | Dauth et al. | |
| 6,183,847 B1 | 2/2001 | Goldwasser | |
| 6,186,996 B1 * | 2/2001 | Martin | 604/385.19 |
| 6,286,145 B1 | 9/2001 | Welchel et al. | |

(Continued)

FOREIGN PATENT DOCUMENTS

CN    1325671 A    12/2001

(Continued)

*Primary Examiner*—Jacqueline F. Stephens
(74) *Attorney, Agent, or Firm*—John P. Colbert; Dara M. Kendall (57) ABSTRACT

The present invention relates to absorbent articles which include one or more components that have been treated with a hydrophobic surface coating intended to render such components impermeable to liquids having relatively low surface tensions.

9 Claims, 5 Drawing Sheets

U.S. PATENT DOCUMENTS

| | | | |
|---|---|---|---|
| 6,306,514 | B1 | 10/2001 | Weikel et al. |
| 6,315,806 | B1 | 11/2001 | Torobin et al. |
| 6,506,180 | B1 | 1/2003 | Lary |
| 6,531,643 | B2 | 3/2003 | Suzuki |
| 6,649,222 | B1 | 11/2003 | D'Agostino et al. |
| 6,695,992 | B2 | 2/2004 | Reneker |
| 6,706,946 | B1 | 3/2004 | Lankhof et al. |
| 6,762,137 | B2 | 7/2004 | Powers et al. |
| 6,803,103 | B2 | 10/2004 | Kauschke et al. |
| 2003/0012910 | A1 | 1/2003 | Galovic |
| 2004/0008078 | A1 | 1/2004 | Kim |
| 2004/0116028 | A1 | 6/2004 | Bryner |
| 2004/0146660 | A1 | 7/2004 | Goodwin et al. |
| 2004/0167479 | A1* | 8/2004 | Warren et al. ............ 604/289 |
| 2005/0177123 | A1 | 8/2005 | Catalan |
| 2006/0058766 | A1* | 3/2006 | Mueller et al. ......... 604/385.19 |

FOREIGN PATENT DOCUMENTS

| | | |
|---|---|---|
| EP | 0 461 484 A | 12/1991 |
| EP | 1 051 958 A | 11/2000 |
| EP | 1 051 958 A1 | 11/2000 |
| EP | 1417945 A1 | 5/2004 |
| JP | 59-005058 A | 1/1984 |
| JP | 10-028700 | 3/1998 |
| WO | WO 95/24173 A2 | 3/1995 |
| WO | WO 02/09491 A2 | 2/2002 |
| WO | WO-2005/077429 A1 | 8/2005 |
| WO | WO 2005/103355 A1 | 11/2005 |
| WO | WO 2005/112854 A1 | 12/2005 |
| WO | WO 01/46505 A2 | 6/2007 |

\* cited by examiner

HYDROPHOBIC SURFACE COATED ABSORBENT ARTICLES AND ASSOCIATED METHODS

CROSS REFERENCE TO RELATED APPLICATIONS

This application claims the benefit of U.S. Provisional Application No. 60/543,785, filed Feb. 11, 2004.

FIELD OF THE INVENTION

The present invention relates to absorbent articles which include one or more components that have been treated with a hydrophobic surface coating intended to render such components impermeable to liquids having relatively low surface tensions.

BACKGROUND OF THE INVENTION

The main purpose of consumer utilization of disposable absorbent articles such as diaper, training pants, sanitary napkins, pantiliners, and adult incontinence articles is to absorb and contain body exudates. Given this purpose, it is quite often the case that such body exudates escape the boundaries of the article as a result of leakage from a point where the article contacts the skin or from seepage through the material that makes up the absorbent article. The latter instance is often caused by the inability of the materials of the article to serve as effective barriers to such bodily fluids.

The undesirable effects of leakage and/or improper containment, difficult cleanup, and/or residual skin contamination are especially evident with regard to fecal matter deposited in a diaper. Feces contained in the diaper can harm the skin of the wearer over time and feces leaking from the diaper almost invariably presents unpleasant, messy clean-ups. Thus, several attempts have been made to add features to diapers such as barriers, pockets, spacers, transverse barriers, apertured topsheets and the like to limit the movement of the fecal material across the topsheet and/or to better confine the fecal matter in the diaper. Such attempts have been generally unsuccessful because they fail to address the fundamental causes of these problems (i.e., the properties of feces) and, because of their cost and complexity. Further, many of the means for isolating or containing feces are directed to fecal material with certain physical properties (e.g., viscosity, free water content and particle size) and are not effective with exudates with physical properties outside a very small range.

Accordingly, it would be desirable to provide an absorbent article with improved low surface energy fluid management capabilities, particularly for feces management. Further, it would be advantageous to provide an economical disposable article with the ability to minimize the negative effects of feces or other viscous bodily waste on the wearer or the caregiver. It would also be advantageous to provide an article which is designed to chemically or physically interact with materials making up the article and in order to reduce the amount of leakage and/or seepage that may occur.

SUMMARY OF THE INVENTION

In order to help resolve at least some of the problems described above, the present invention provides an article which comprises:

a. a liquid pervious first topsheet having an interior surface and an exterior surface;

b. a backsheet having an interior surface and an exterior surface wherein said backsheet is attached to said topsheet along a periphery;

c. an absorbent core disposed between said topsheet and said backsheet;

d. an additional article component selected from the group consisting of a core cover, a diaper outer cover, an ear, a first cuff, a second cuff, a belt, a wing, an elasticized topsheet, and combinations thereof; wherein said component has an interior and an exterior surface; and e. a hydrophobic surface coating disposed on at least one surface of said backsheet or said additional article component wherein said coating comprises one or more silicone polymers and wherein said coating is substantially free of aminosilicones.

DETAILED DESCRIPTION OF THE INVENTION

For the present invention, detailed herein are various definitions which are intended to aid in the interpretation of the claimed subject matter.

As used herein, the term "absorbent article" refers to devices which absorb and contain body exudates, and more specifically, refers to devices which are placed against or in proximity to the body of the wearer to absorb and contain the various exudates discharged from the body. Such devices include, but are not limited to, diapers, training pants, adult incontinence products, sanitary napkins, and pantiliners.

As used herein, the term "diaper" refers to an absorbent article generally worn by infants, and incontinent persons that is worn about the lower torso of the wearer. In other words, the term "diaper" includes infant diapers, training pants, adult incontinence devices, etc.

As used herein, the term "disposable" refers to absorbent articles which generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "telomer" refers to an addition polymer, usually of low molecular weight, in which the growth of molecules is terminated by a radical-supplying chain transfer agent or a low molecular weight polymer in which the terminal group on the end of the chain-like molecule is not the same as the side group. Telomer may also be used synonymously with oligomer, which is a polymer with very few (two to ten) repeating units.

As used herein, the term "disposed" is used to mean that an element(s) of the diaper is formed (joined or positioned) in a particular place or position as a unitary structure with other elements of the diaper or as a separate element joined to another element of the diaper.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.)

A "unitary" absorbent article refers to absorbent articles which are formed of separate parts united together to form a coordinated entity so that they do not require separate manipulative parts like a separate holder and liner.

As used herein, the term "comprising" means that the various components, ingredients, or steps, can be conjointly employed in practicing the present invention. Accordingly, the term "comprising" encompasses the more restrictive terms "consisting essentially of" and "consisting of."

All percentages, ratios and proportions used herein are by weight unless otherwise specified.

Absorbent Article

The disposable absorbent articles of the present invention comprise a liquid pervious first topsheet, a backsheet attached or joined to the topsheet and an absorbent core positioned between the topsheet and the backsheet. Disposable absorbent articles and components thereof, including the topsheet, backsheet, absorbent core, and any individual layers of these components, have an interior surface (or body surface) and an exterior surface (or garment surface). As used herein, "interior surface" or "body surface" means that surface of the article or component which is intended to be worn toward or adjacent to the body of the wearer, while the "exterior surface" or "garment surface" is on the opposite side and is intended to be worn toward or placed adjacent to the undergarments when the disposable absorbent article is worn.

The following description generally discusses the absorbent core, first topsheet, and backsheet materials that are useful in disposable absorbent articles. It is to be understood that this general description applies to these components of the specific absorbent article shown in FIG. 1 and further described below, in addition to those of other disposable absorbent articles which are generally described herein.

Figure 1:
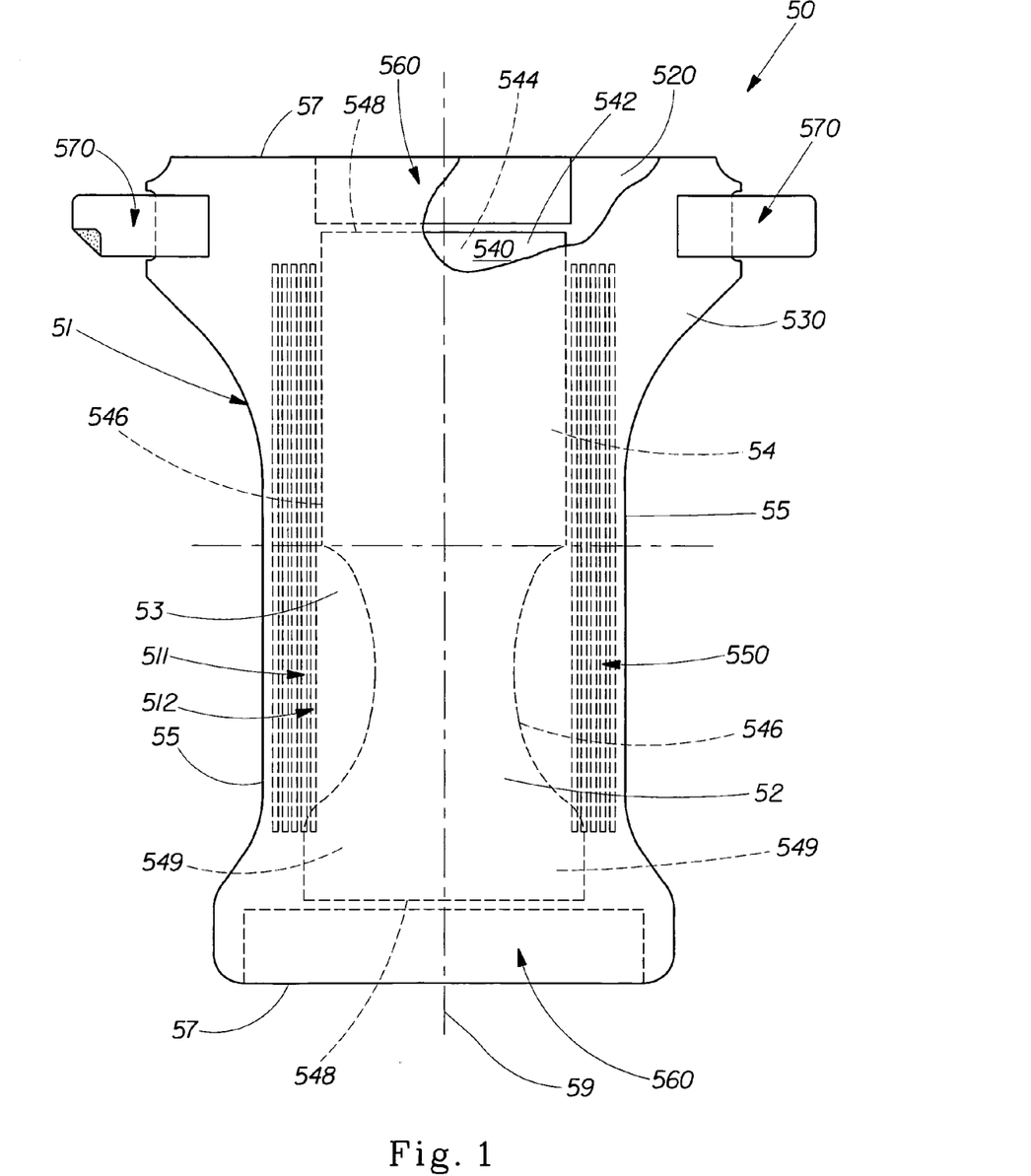
FIG. 1 shows a plan view of the absorbent article of the present invention.

FIG. 1 is a plan view of the diaper 50 of the present invention in its flat-out, uncontracted state (i.e., with elastic induced contraction pulled out) with portions of the structure being cut-away to more clearly show the construction of the diaper 50 and with the portion of the diaper 50 which faces away from the wearer, the outer surface, oriented towards the viewer. As shown in FIG. 1, the diaper 50 preferably comprises a liquid pervious first topsheet 520; a liquid impervious backsheet 530 joined with the topsheet 520; an absorbent core 540 positioned between the first topsheet 520 and the backsheet 530, the absorbent core 540 having a exterior surface (or garment facing surface) 542, an interior surface (or a body facing surface) 544, side edges 546, waist edges 548, and ears 549. The diaper 50 preferably further comprises a first cuff 550, a second cuff 511, and an additional cuff 512; an elastic waist feature multiply designated as 560 (also referred to herein as a waistband or belt); and a fastening system generally multiply designated as 570.

The diaper 50 is shown in FIG. 1 to have an outer surface 52, an inner surface 54 opposed to the outer surface 52, a first waist region 56, a second waist region 58, and a periphery 51 which is defined by the outer edges of the diaper 50 in which the longitudinal edges are designated 55 and the end edges are designated 57. (While the skilled artisan will recognize that a diaper is usually described in terms of having a pair of waist regions and a crotch region between the waist regions, in this application, for simplicity of terminology, the diaper 50 is described as having only waist regions including a portion of the diaper which would typically be designated as part of the crotch region). The inner surface 54 of the diaper 50 comprises that portion of the diaper 50 which is positioned adjacent to the wearer's body during use (i.e., the inner surface 54 generally is formed by at least a portion of the first topsheet 520 and other components that may be joined to the first topsheet 520). The outer surface 52 comprises that portion of the diaper 50 which is positioned away from the wearer's body (i.e., the outer surface 52 generally is formed by at least a portion of the backsheet 530 and other components that may be joined to the backsheet 530). (As used herein, the portion of the diaper 50 or component thereof which faces the wearer is also referred to as the body facing surface. Similarly, the portion facing away from the wearer is also referred to herein as the garment facing surface.) The first waist region 56 and the second waist region 58 extend, respectively, from the end edges 57 of the periphery 51 to the lateral centerline 53 of the diaper 50. FIG. 1 also shows the longitudinal centerline 59.

Figure 2:
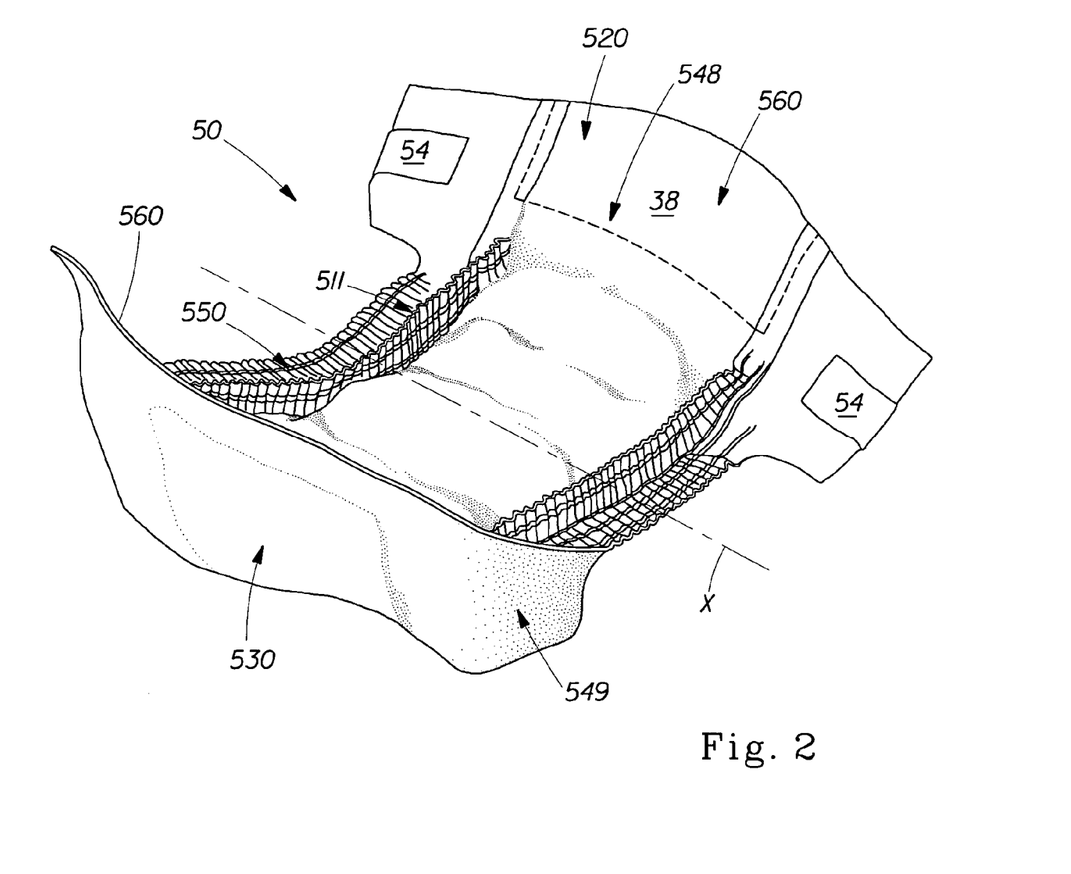
FIG. 2 shows a perspective view of an absorbent article of the present invention.
Figure 3:
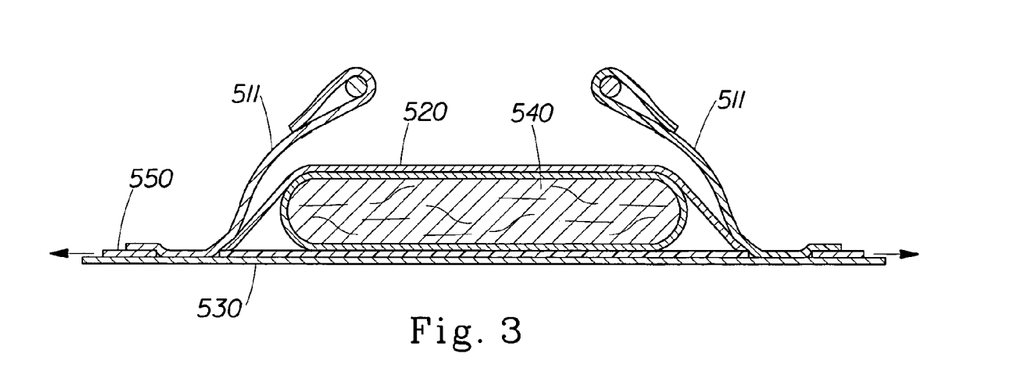
FIG. 3 shows a cross-sectional view of the absorbent article depicted in FIG. 2.

FIG. 2 shows a perspective view of the article of the present invention which includes at least a first and second cuff wherein the backsheet and at least one of the additional components has been treated with the hydrophobic surface coating. FIG. 3 merely depicts a cross-sectional view of the diaper shown in FIG. 2.

Absorbent Core

The absorbent core 540 may take on any size or shape that is compatible with the diaper 50. One preferred embodiment of the diaper 50 has an asymmetric, modified T-shaped absorbent core 540 having ears in the first waist region but a generally rectangular shape in the second waist region. Exemplary absorbent structures for use as the absorbent core of the present invention that have achieved wide acceptance and commercial success are described in U.S. Pat. Nos. 4,610, 678, 4,673,402, 4,888,231, and 4,834,735. The absorbent core may further comprise the dual core system containing an acquisition/distribution core of chemically stiffened fibers positioned over an absorbent storage core as detailed in U.S. Pat. Nos. 5,234,423 and 5,147,345.

In general, the absorbent core is capable of absorbing or retaining liquids (e.g., menses, urine, and/or other body exudates). The absorbent core is preferably compressible, conformable, and non-irritating to the wearer's skin. The absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core may have varying caliper zones and/or have a profile so as to be thicker in the center; hydrophilic gradients; gradients of the absorbent composite of the present invention, superabsorbent gradients; or lower average density and lower average basis weight zones, e.g., acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as diapers, incontinence pads, pantiliners, regular sanitary napkins, and overnight sanitary napkins, and to accommodate wearers ranging from infants to adults. The absorbent core can include other absorbent components that are often used in absorbent articles, for example, a dusting layer, a wicking or acquisition layer, or a secondary (e.g., an elasticized) topsheet for increasing the wearer's comfort.

Topsheet

The first topsheet 520 of diaper 50 is preferably made of a hydrophilic material that promotes rapid transfer of liquids (e.g., urine, menses, and/or runny feces) through the topsheet. If the first topsheet is made of a hydrophobic material, at least the upper surface of the topsheet is treated to be hydrophilic so that liquids will transfer through the topsheet more rapidly. This diminishes the likelihood that body exudates will flow off the topsheet rather than being drawn through the topsheet and being absorbed by the absorbent core. The first topsheet can be rendered hydrophilic by treating it with a surfactant. Suitable methods for treating the topsheet with a surfactant include spraying the topsheet material with the surfactant and immersing the material into the surfactant. A more detailed discussion of such a treatment and hydrophilicity is contained in U.S. Pat. Nos. 4,988,344 and 4,988,345.

The topsheet is preferably pliant, soft feeling, and non-irritating to the wearer's skin. Further, the topsheet is liquid pervious, permitting liquids (e.g., menses, urine, and/or runny feces) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

Figure 7:
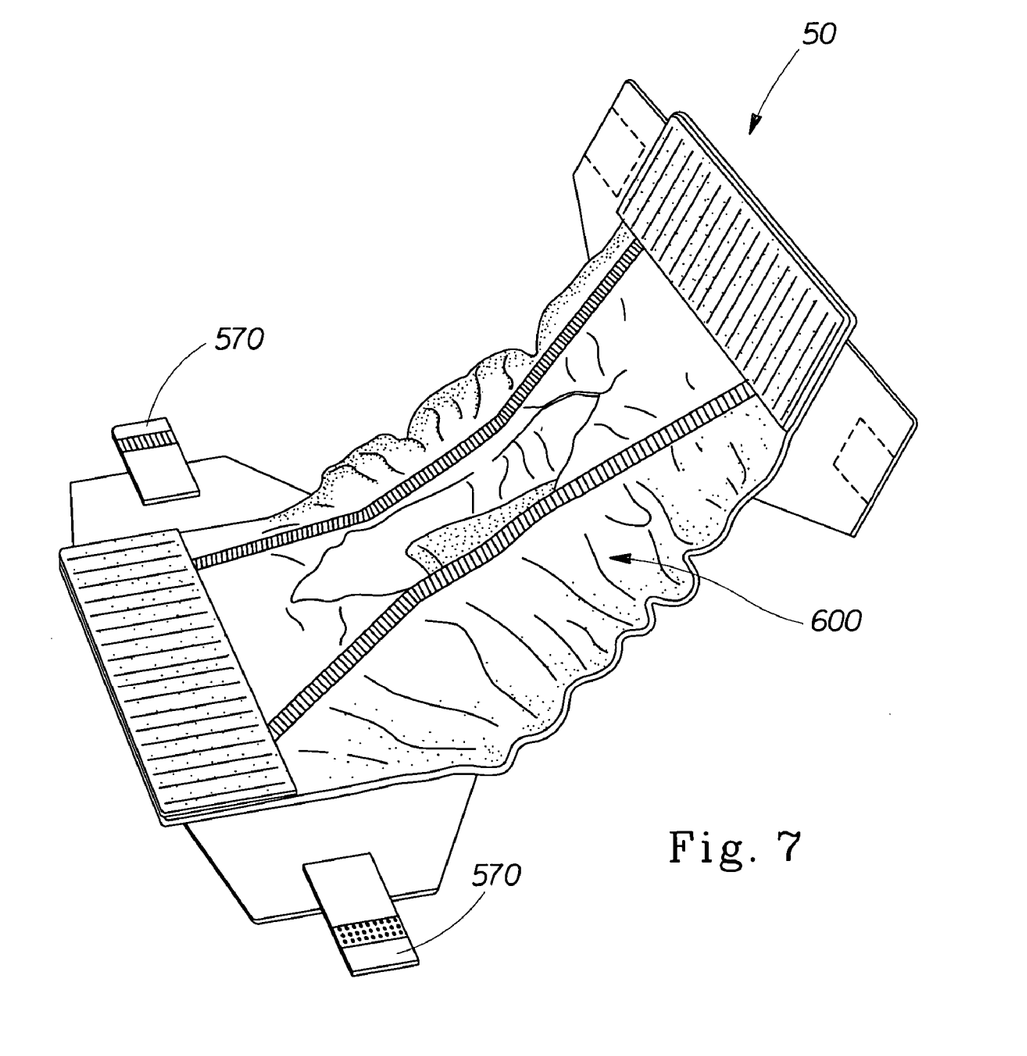
FIG. 7 illustrates via a perspective view another embodiment of the present invention in which the hydrophobic surface coating has been applied to at least an elasticized topsheet of an absorbent article.

Additionally, articles according to the present invention may comprise topsheets that are elasticized to provide storage compartments for body exudates, particularly bowel movements. Such topsheets and articles containing them are detailed in U.S. Pat. No. 6,482,191. Such an elasticized topsheet 600 is shown in FIG. 7 in an additional embodiment of the present invention.

Backsheet

The backsheet is preferably impervious to low surface tension fluids (e.g., menses, urine, and/or runny feces). As used herein, "low surface tension fluids" refers to fluids having a surface tension of less than about 72 dynes/cm, preferably less than about 60 dynes/cm, and even more preferably less than about 55 dynes/cm, and most preferably from about 25 to about 55 dynes/cm. The backsheet is preferably manufactured from a thin plastic film, although other flexible liquid impervious materials may also be used. As used herein, the term "flexible" refers to materials which are compliant and that readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. A suitable backsheet is a polyethylene film having a thickness of from about 0.012 mm (0.5 mils) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385. The backsheet is preferably embossed and/or matte finished and provides a more clothlike-appearance. Further, the backsheet may permit vapors to escape from the absorbent core (i.e., the backsheet is breathable) while still preventing exudates from passing through the backsheet. The size of the backsheet is dictated by the size of the absorbent core and the exact absorbent article design selected.

The backsheet and the first topsheet are positioned adjacent the garment surface and the body surface, respectively, of the absorbent core. The absorbent core is preferably joined with the topsheet, the backsheet, or both in any manner as is known by attachment means (not shown in FIG. 1) such as those well known in the art. However, embodiments of the present invention are envisioned wherein portions of the entire absorbent core are unattached to one or both of the topsheet and the backsheet.

For example, the backsheet and/or the first topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by Bostik-Findley of Milwaukee, Wis. under the designation HL-24012031. The attachment means will preferably comprise an open pattern network of filaments of adhesive as is disclosed in U.S. Pat. No. 4,573,986, issued to Minetola, et al. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr.; U.S. Pat. No. 4,785,996 issued to Zwieker, et al.; and U.S. Pat. No. 4,842,666 issued to Werenicz. Alternatively, the attachment means may comprise heat bonds, pressure bonds, ultrasonic bonds, dynamic mechanical bonds, or any other suitable attachment means or combinations of these attachment means as are known in the art.

Additional Components

In a preferred embodiment, the diaper 50 further comprises at least a first cuff 550 for providing improved containment of liquids and other body exudates; an elastic waist feature 560 that provides improved fit and containment; and a fastening system 570 which forms a side closure which maintains the first waist region 56 and the second waist region 58 in an overlapping configuration such that lateral tensions are maintained around the circumference of the diaper to maintain the diaper on the wearer. The diaper 50 may also comprise elasticized side panels (not shown) in the waist regions 56 and 58 to provide an elastically extensible feature that provides a more comfortable and contouring fit and more effective application of the diaper 50.

The elasticized leg cuffs 550 can be constructed in a number of different configurations, including those described in U.S. Pat. Nos. 3,860,003, 4,636,207, 4,695,278, 4,704,115, 4,795,454, 4,900,317, 4,909,803 (Reissued as USRE34,920), 5,085,654, 5,492,751, 6,476,288 and SIR H1,630.

For example, diaper 50 may include one or more first cuffs 550 which provide improved containment of liquids and other body exudates. First cuffs 550 may also be referred to as outer leg cuff, leg bands, side flaps, leg cuffs or elastic cuffs. U.S. Pat. No. 3,860,003 describes a disposable diaper which provides a contractible leg opening having a side flap and one or more elastic members to provide an elasticized leg cuff.

Additionally, diaper 50 may include one or more second cuffs 511 which also provide improved containment of liquids and other body exudates. Second cuffs 511 may also be referred to as barrier leg cuffs, inner leg cuffs or "stand-up" elasticized flaps. U.S. Pat. Nos. 4,808,178 and 4,909,803 issued to Aziz et al. on Feb. 28, 1989 and Mar. 20, 1990, respectively, describe disposable diapers having "stand-up" elasticized flaps that improve the containment of the leg regions.

First cuff 550 and second cuff 511 may both be provided by way of a dual cuff, as exampled in U.S. Pat. Nos. 4,695,278 and 4,795,454 issued to Lawson on Sep. 22, 1987 and to Dragoo on Jan. 3, 1989, respectively.

Additional cuffs 512 may be provided in an article of the present invention as detailed in U.S. Statutory Invention Registration H1630, which published Jan. 7, 1997.

FIG. 2 shows a perspective diagram of a diaper according to the present invention which includes at least one or more first and second cuffs wherein at least one of the cuffs has been coated with the hydrophobic surface coating.

FIG. 3 depicts a cross-sectional view of the diaper shown in FIG. 2. In certain embodiments, the second cuff may not be necessary due to the use of the hydrophobic coating on the first cuff.

The elasticized waist feature preferably comprises an elasticized waistband (not shown) that may be constructed in a number of different configurations including those described in U.S. Pat. Nos. 4,515,595, 5,026,364, and 5,151,092. This waistband or belt of the diaper or absorbent article may include a cutout of some sort that allows for undisturbed placement of an infant's navel, which tends to be sensitive for a time after birth. Preferably, this cutout is in the shape of a semicircle but may be in any geometric shape that allows for a comfortable fit of the infant's navel.

The elasticized side panels may be constructed in a number of configurations. Examples of diapers with elasticized side panels positioned in the ears (or ear flaps) of the diaper are disclosed in U.S. Pat. Nos. 4,857,067, 4,381,781, 4,938,753, and 5,151,092.

Exemplary fastening systems 570 are disclosed in U.S. Pat. Nos. 4,846,815, 4,894,060, 4,946,527, 3,848,594, 4,662,875, and 5,151,092.

Hydrophobic Surface Coating

The disposable absorbent articles of the present invention additionally comprise a hydrophobic surface coating that is disposed on at least one surface of one or more of the various components of the article including, but not limited to, a core cover, a diaper outer cover, an ear, a wing, belt, a backsheet, a first cuff, a second cuff, and even combinations thereof. This hydrophobic surface coating comprises one or more silicone polymers and is also substantially free of aminosilicones.

Suitable silicone polymers are selected from the group consisting of silicone MQ resins, polydimethysiloxanes, crosslinked silicones, silicone liquid elastomers, and combinations thereof. Typically, the molecular weight of such silicone polymers should be at least about 4000 $M_W$, preferably at least about 10,000 $M_W$, more preferably at least about 15,000 $M_W$, even more preferably at least about 20,000 $M_W$, and most preferably at least about 25,000 $M_W$. Preferred polydimethylsiloxanes are selected from the group consisting of vinyl-terminated polydimethsiloxanes, methyl hydrogen dimethylsiloxanes, hydroxyl-terminated polydimethysiloxanes, organo-modified polydimethylsiloxanes, and combinations thereof.

Alternatively, fluorinated polymers may also be used. Suitable fluorinated polymers are selected from the group consisting of telomers and polymers containing tetrafluoroethylene and/or perfluorinated alkyl chains. For instance, fluorinated surfactants, which are commercially available from Dupont under the tradename Zonyl®, are suitable for use herein. In particular, Zonyl® 321, 329, 8740, 9027, and 9360 are well suited for use in the present invention. Additionally, other Zonyl® materials include fluroadditives like micro-powders may be useful herein. These include, but are not limited to Zonyl® MP1100, MP1200, MP1400, MP1500J, MP1600N, TE-3667N (which is a water dispersion).

Figure 4:
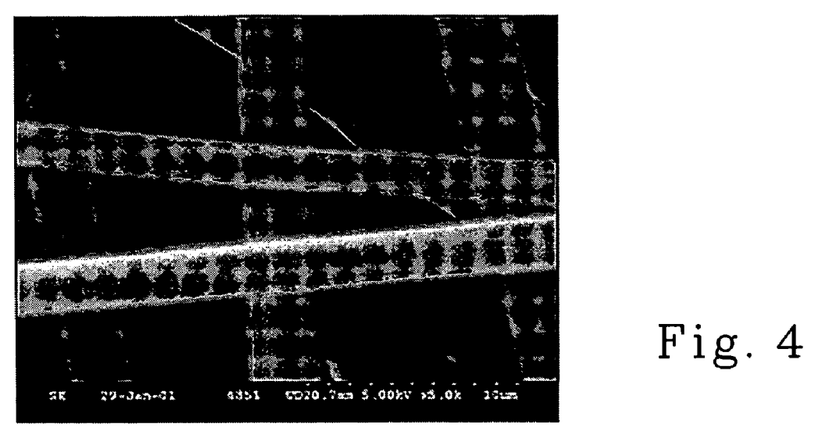
FIG. 4. illustrates a component of the present article prior to treatment with the hydrophobic surface coating of the present invention.
Figure 5:
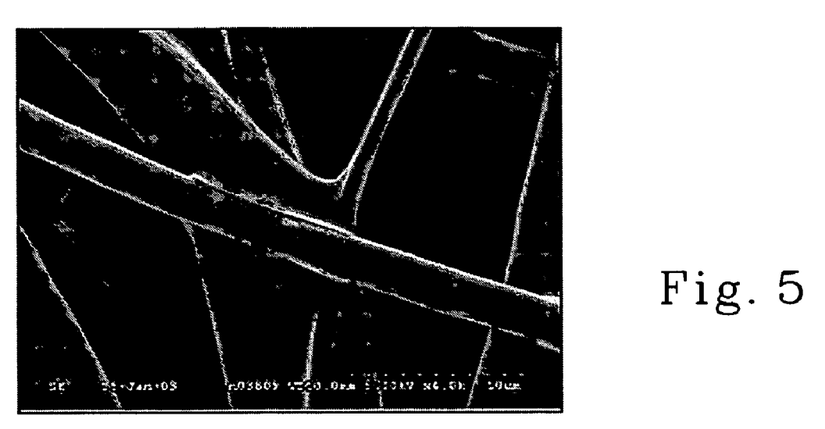
FIG. 5 illustrates a component of an article of the present invention that has been treated with a hydrophobic surface coating according to the present invention.
Figure 6:
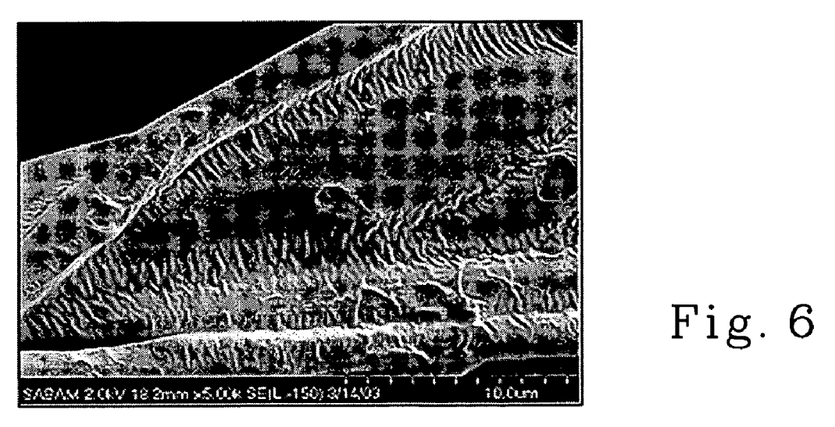
FIG. 6 illustrates a component of an article of the present invention that has been treated with another hydrophobic surface coating according to the present invention.

Without being limited by theory, Applicants have found that these hydrophobic surface coatings, when applied to various absorbent article components, tend to envelope or at least partially coat one or more fibrous structures of the component in such a way that a cohesive, uniform film-like network is formed around the fibrous structures, and partially fills the pore network of the fibrous structures. This film-like network serves to increase the barrier properties of the component, particularly when exposed to low surface energy fluids. The film-like network is illustrated in FIGS. 4, 5, and 6. In FIG. 4, an uncoated 15 gsm fibrous meltblown nonwoven is depicted. In FIG. 5, the nonwoven of FIG. 4 has been treated with a hydrophobic surface coating known as PSA950, which is commercially available from GE Silicones. PSA950 is a pressure sensitive adhesive which is a phenyl siloxane in solvent. Here, the film-like network has formed between the fibrous structures of the nonwoven. Likewise, in FIG. 6, the uncoated meltblown nonwoven of FIG. 4 is coated with a hydrophobic surface coating known as C2-0563 fabric water repellant, which is commercially available from Dow Corning. Again, it is clear that a film-like network is formed between the fibers and in the pores of the nonwoven, thereby improving its barrier properties.

In certain embodiments of the present invention, the coating may be inherently elastomeric. Accordingly, when deposited onto one or more surfaces of an absorbent article component, the hydrophobic surface coating may additionally provide an elastic character to the article component when stretched.

Additionally, although it is envisioned that the present invention is primarily directed to absorbent personal care articles, it is easily foreseeable that the hydrophobic surface coatings disclosed herein may also be disposed onto substrates utilized for other purposes. For instance, treated substrates could be utilized in the manufacture of various surgical or medical materials (e.g., gowns, drapes, shoe covers, and caps), wipes (e.g., for car cleaning, lens cleaning, packaging, wet cleaning, and dust), consumer clothing, etc.

Moreover, it is important to note that when the coating is deposited onto the article component, it is preferred that the component is substantially free of polymers containing melt additives selected from the group consisting of polydimethylsiloxanes, guerbet esters, and combinations thereof.

Test Methods

Liquid Strike Through

The barrier performance of the coated substrates is determined by measuring the time in which a liquid added to the surface of the substrate penetrates the surface of the substrate. The test method conforms to the Edana method 150.4-99 using a Lister SN L5725 Model 1998 with the following changes:

1. Reference absorbent pad consists of 10 layers of filter paper (100 mm×100 mm Ahlstrom Grade 989) supplied by Empirical Mfg. Co., Inc. (Cincinnati, Ohio 513-948-1616).
2. Simulated runny BM/urine fluid mixture consisting of 0.04% (w/v) tRiton-X-100 (CAS# 9002-93-1) aqueous solution with a surface tension of approximately 32±mN/m.
3. Prior to the start of each test, and in between each replicate, the Lister electrodes are rinsed with a 0.9% NaCl aqueous solution.

An average liquid strike through is determined by dividing the sum of times by the number of component samples that are tested. Typically, the number of samples will be about 30, i.e., n=30.

In order to determine the increase of liquid strike through time that results, a comparison is done of average liquid strike through time of coated samples versus uncoated (or untreated) samples.

EXAMPLES

Example 1

A hydrophobic surface coating of the present invention is prepared by spraying, dipping, or employing a kiss-roll process of an aqueous mixture of vinyl terminated polydimethylsiloxane and methylhydrogen polydimethylsiloxane in a 30:1 ratio in order that the coating is deposited on the substrate. Substrate nonwovens used in this example were 13 gsm, 15 gsm, 17 gsm, 20 gsm, 30 gsm, and 34 gsm spun/melt/spun polypropylene nonwovens, and 15 gsm and 20 gsm melt polypropylene nonwovens, which are commercially available from various suppliers. The aqueous mixture also contains a transition metal catalyst to facilitate the self-crosslinking of the PDMS polymers. The wet coated substrate is dried at 90° C.-120° C. for 0.1-1.0 minutes depending if the sample is coated via a commercial or laboratory coating process and is then stored in a suitable container for later use.

Example 2

A nonwoven diaper cuff component treated with a hydrophobic surface coating is prepared. A 10% solution of a vinyl terminated PDMS (commercially available from GE Silicones as SM3200) and a methyl hydrogen PDMS (commercially available from GE Silicones as SM3010) is prepared and mixed for 30 minutes. A typical cuff component (spun-melt nonwoven, as detailed in U.S. Pat. No. 5,492,751, is dipped into the solution and the excess liquid squeezed out via calendar roll and the component dried in an air convection oven at a temperature of 90° C.-120° C. for a time no more than 45 seconds in order that the coating is deposited on the substrate. The cuff material is incorporated into a diaper as detailed in U.S. Pat. Nos. 3,860,003, 4,636,207, 4,695,278, 4,704,115, 4,795,454, 4,900,317, 4,909,803 (Reissued as USRE34,920), 5,085,654, 5,492,751, 6,476,288 and SIR H1,630.

Example 3

A nonwoven diaper cuff and/or backsheet component treated with a hydrophobic surface coating is prepared. A 10% solution of a hydroxyl terminated PDMS (commercially available from GE Silicones as SM2245) and a methyl hydrogen PDMS (commercially available from GE Silicones as SM2014c) is prepared and mixed for 30 minutes. The cuff and/or backsheet component, comprised of spun-melt nonwoven as detailed in U.S. Pat. No. 5,492,751, is dipped into the solution and the excess liquid squeezed out via calendar roll and the component dried in an air convection oven at a temperature of 90° C.-120° C. for a time no more than 45 seconds in order that the coating is deposited on the substrate and incorporated into a diaper as detailed in U.S. Pat. Nos. 3,860,003, 4,636,207, 4,695,278, 4,704,115, 4,795,454, 4,900,317, 4,909,803 (Reissued as USRE34,920), 5,085,654, 5,492,751, 6,476,288 and SIR H1,630.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a. a liquid pervious first topsheet having an interior surface and an exterior surface;
   b. a backsheet having an interior surface and an exterior surface wherein said backsheet is attached to said topsheet along a periphery;
   c. an absorbent core disposed between said topsheet and said backsheet;
   d. an additional article component selected from the group consisting of a core cover, a diaper outer cover, an ear, a first cuff, a second cuff, a belt, a wing, an elasticized topsheet, and combinations thereof; wherein said component has an interior and an exterior surface; and
   e. a hydrophobic surface coating disposed on at least one surface of said backsheet or said additional article component such that the hydrophobic surface coating forms a film on at least a portion of the coated surface and increases the barrier properties of the surface; wherein said coating comprises a mixture of at least two silicone polymers having a molecular weight of at least about 15,000 $M_w$ and wherein said silicone polymers are polydimethylsiloxanes selected from the group consisting of vinyl-terminated polydimethsiloxanes, methyl hydrogen dimethylsiloxanes, hydroxyl-terminated polydimethysiloxanes, and combinations thereof and wherein said coating is substantially free of aminosilicones.

2. The article of claim 1 wherein said coating is disposed on said interior surface of said backsheet or said additional article component.

3. The article of claim 1 wherein said coating increases the average liquid strikethrough time at least about 2 seconds over the average liquid strikethrough of an untreated component.

4. The article of claim 1 wherein the article component onto which said coating is disposed is substantially free of polymers containing melt additives selected from the group consisting of polydimethylsiloxanes, guerbet esters, and combinations thereof.

5. The article of claim 1 wherein said article further comprises a cutout in the waist feature for positioning of an infant's navel.

6. The article of claim 1 wherein said additional article component is a first cuff and wherein said cuff is disposed along the periphery of said backsheet and said topsheet.

7. A method of increasing the hydrophobicity of an absorbent article component, said method comprising the step of depositing on said component a hydrophobic coating such that the hydrophobic coating forms a film on at least a portion of the coated component and increases the barrier properties of the surface; wherein said coating comprises a mixture of at least two silicone polymers having a molecular weight of at least about 15,000 $M_w$ and wherein said silicone polymers are polydimethylsiloxanes selected from the group consisting of vinyl-terminated polydimethsiloxanes, methyl hydrogen dimethylsiloxanes, hydroxyl-terminated polydimethysiloxanes, and combinations thereof and wherein said coating is substantially free of aminosilicones.

8. A disposable substrate article comprising:
a. a substrate;
b. a hydrophobic surface coating disposed on at least one surface of said substrate such that the hydrophobic surface coating forms a film on at least a portion of the coated surface and increases the barrier properties of the surface; wherein said coating comprises a mixture of at least two silicone polymers having a molecular weight of at least about 15,000 $M_w$ and wherein said silicone polymers are polydimethylsiloxanes selected from the group consisting of vinyl-terminated polydimethsiloxanes, methyl hydrogen dimethylsiloxanes, hydroxyl-terminated polydimethysiloxanes, and combinations thereof and wherein said coating is substantially free of aminosilicones.

9. The article of claim 8 wherein said article is selected from the group consisting of disposable garments, wiping cloths, cleaning cloths, shoe covers, packing materials, drapes, and combinations thereof.

* * * * *